United States Patent
Rabinski et al.

(10) Patent No.: US 7,064,826 B2
(45) Date of Patent: Jun. 20, 2006

(54) DIGITAL OPTICAL MEASUREMENT OF PARTICLE POPULATIONS USING REDUCED MAGNIFICATION

(75) Inventors: Guenadi Rabinski, Ottawa (CA);
Serge Emile LeBlanc, Ottawa (CA);
Frederick David King, Richmond (CA)

(73) Assignee: Brightwell Technologies, Stittsville (CA)

( * ) Notice: Subject to any disclaimer, the term of this patent is extended or adjusted under 35 U.S.C. 154(b) by 308 days.

(21) Appl. No.: 10/653,133

(22) Filed: Sep. 3, 2003

(65) Prior Publication Data
US 2005/0046841 A1    Mar. 3, 2005

(51) Int. Cl.
*G01N 15/02* (2006.01)
(52) U.S. Cl. ...................................... 356/335
(58) Field of Classification Search ............ None
See application file for complete search history.

(56) References Cited

U.S. PATENT DOCUMENTS 5,282,151 A * 1/1994 Knollenberg ............ 702/26
6,091,492 A * 7/2000 Strickland et al. .......... 356/336
2001/0035954 A1 * 11/2001 Rahn et al. .................. 356/336
2002/0084172 A1 * 7/2002 Toms ........................ 198/445

OTHER PUBLICATIONS

Michael Schäfer, "Digital optics: Some Remarks on the Accuracy of Particle Image Analysis", Part. Part. Syst. Charact. 19 (2002) pp. 158-168.

* cited by examiner

Primary Examiner—Michael P. Stafira
(74) Attorney, Agent, or Firm—Teitelbaum & MacLean; Neil Teitelbaum; Doug MacLean

(57) ABSTRACT

The present invention relates to a method for determining a distribution of a parameter, e.g. cross-sectional area, of a particle population for identifying specific types of particles therein. A plurality of images of the particles are detected on a pixel array and a number of pixels in the form of a pixel count is determined for each of the plurality of images of particles. Weighting factors, e.g. a probability which relate values of the parameter to different pixel counts are used to determine the distribution for the parameter of the particle population. The method depends on the facts that the total population to be analyzed contains many particles and is uniformly distributed, over many frames, throughout the optical sampling volume, and that even when substantial uncertainty exists on the parameter value corresponding any individual image, the statistical information which is obtained from many images may be used to provide accurate distributions.

9 Claims, 1 Drawing Sheet

DIGITAL OPTICAL MEASUREMENT OF PARTICLE POPULATIONS USING REDUCED MAGNIFICATION

FIELD OF THE INVENTION

This invention relates generally to deriving a distribution of a characteristic of a population of particles within a volume of a sample of a fluid.

BACKGROUND OF THE INVENTION

Many prior art systems exist for detecting the presence of particles or size of particles in a fluid, such as a supply of potable water. For example, U.S. Pat. No. 5,438,408 entitled Measuring Device and Method for the Determination of Particle Size Distributions by Scattered Light Measurements discloses the use of a charge coupled device (CCD) camera. U.S. Pat. No. 6,061,130 entitled Apparatus for Determining the Particle Size Distribution of a Mixture discloses an apparatus that includes a CCD matrix. By identifying particles by predetermined parameters, such as diameter or cross-sectional area, such systems can ascertain the presence or absence of unwanted harmful bacteria in a water sample which are known to be within a predetermined range of diameters.

Some of these systems have also been known to be useful in analyzing other fluids such as blood and blood products. Typically, identifying particle populations in accordance with some parameter, for instance particle size or particle cross-section, allows a parameter distribution to be ascertained. In a water supply the goal may be to determine the number of particles of various sizes that are present in a representative sample.

Detection systems most often employ the use of computers or powerful processor-based systems coupled to one or more CCD or pixel arrays of detecting elements, which detect the presence of one or more particles projected upon a portion of the array of charge coupled elements. Most often thousands of frames of information are collected. Within a single frame more than a single particle may be detected; therefore, the software is programmed to find clusters of pixels, indicating the presence of a particle. Some software can determine instances where portions of particles overlap and determine the size of each particle.

In each successive frame, images of the particles contained within an optical sampling volume are projected onto the pixel array. These images of the particles are randomly distributed on the array depending on the positions of the particles in the sampling volume. In order to determine the value of a parameter of the particle, for example the cross-sectional area of a particle, the number of pixels in the particle image corresponding to that parameter covered, wholly or partially, is counted and a scaling factor is applied. Subsequently, a table is compiled of the number of counts corresponding to each pixel total as the images in each frame are analyzed. For example 90 pixels: 350 counts, implies that there are 350 instances of 90 pixels being at least partially covered by a particle, or stated differently, in the total number of frames analyzed, there are 350 instances of 90 detectors within the array sensing the presence of at least a portion of a particle; correspondingly, 91 pixels: 410 counts, indicates 91 detectors within the array sensed the presence of at least a particle in 410 separate instances. In order to produce the parameter distribution information, the parameter value corresponding to each pixel total must be determined. When the number of pixels is large, a simple scaling factor, which depends only on the pixel size and the magnification, gives accurate results. However when the number of pixels is small, that is, when only very few detectors sense the presence of at least a portion of a particle, this scaling factor becomes increasingly uncertain because of the image location error. Image location error results from the fact that the pixel total measured for a particular value of a particle image depends on the location of the image with respect to the pixel grid. This can be understood more clearly with reference to FIG. 1, where two particles P1 and P2 having a same cross-sectional area are shown superimposed over a pixel array. If the threshold of the array is set to its most sensitive, any partial coverage of an array element or pixel by a portion of a particle will trigger that array element to detect the presence of a particle. Particle P1 on the left of the array happens to be positioned such that it at least partially covers 9 pixels. Particle P2 on the other hand, being the same size as particle P1 at least partially covers or triggers 16 pixels at a different location on the CCD detector array. Of course, whether a partially covered pixel triggers an array element depends upon the threshold setting.

If a particle image is very large compared to the size of a pixel, for example covering 200 pixels, the variation in pixel total with location will be small, and will likely only vary a few percent with location. However the variation in pixel total is very large and in the neighborhood of 50% in the example described heretofore, where a same pixel is measured to be 16 pixels in cross-section in one instance and 9 pixels in cross section in another instance.

For in-line operation or, in applications where a large number of samples must be analyzed, it is desirable that measurements be made in the shortest possible time. For example it would be desirable to analyze a sample in several minutes and not in several hours. Furthermore, it is desirable that a single measurement at a single magnification provides information, i.e. the number of particles in each of a specified range of equivalent diameters for the particles having the largest possible range of sizes. To ensure that the image location error is small, a sufficiently high magnification may be selected so that the images of the smallest particles occupy a sufficient number of pixels. Approximately 200 are required to reduce equivalent diameter measurement errors to ±6%. However, as magnification is increased, the optical sampling volume becomes smaller. By way of example: the time required to analyze a typical sample of 1 cc, using a magnification such that a 2.5 micron particle occupies two hundred 7.5×7.5 micron pixels, is approximately 5 hours. Furthermore as magnification is increased, the size of the largest particle, which may be imaged without incurring a significant probability that its image will overlap with the edge of the pixel array, is reduced; for the magnification value used in the example, this upper limit is approximately 50 microns.

If the problem of location error could be obviated, for maximum measurement speed and maximum parameter measurement range it is desirable that parameter distributions can be measured using the smallest possible number of pixels in the image of the smallest particle to be included in the characterization of the population.

It is an object of this invention, to provide a relatively fast and inexpensive system whereby a small number of pixels can be used to image a particle without significantly suffering from the effects of the location error normally associated with using a small number of pixels.

SUMMARY OF THE INVENTION

In accordance with the invention, a method is provided for determining a distribution of a parameter of a particle population comprising the steps of:

a) detecting on a pixel array of elements a plurality of images of the particles;

b) determining a number of pixels in the form of a pixel count corresponding to each of the plurality of images of particles;

c) determining a plurality of weighting factors or probabilities which relate values of the parameter of a particle to different pixel counts; and, d) utilizing the plurality of counts and the weighting factors to determine the distribution for the parameter of the particle population In accordance with the invention, in a system for analyzing a parameter in a system for analyzing a parameter in a particle population in a fluid, wherein particles are substantially randomly distributed, and particles range in value from $X_1$ to $X_{10}$, in increments, values of $X_1$ through $X_{10}$ being different values, there is further provided a method of determining a total number of particles within a sampled volume having a predetermined parameter value, comprising the steps of:

a) using a detector array of pixels to detect a plurality of images of the particles;

b) counting a number of pixels $Y_1, Y_2, Y_3$, through at least $Y1_0$ corresponding to each of the plurality of images of particles;

c) determining a plurality of weighting factors $P(X_M;Y_N)$ corresponding to different pixel counts from $Y_1$ through at least $Y_{10}$, wherein $P(X_M;Y_N)$=the probability of a particle with a parameter value $X_M$ will occupy a pixel total $Y_N$ wherein M can take on values from 1 through at least 10 and X can take on values from at least 1 through 10 d) determining $D(X_M)$=the total number of particles within the volume sampled having a parameter value $X_M$, by solving a set of linear equations of the form:

$$Y_1 = D(X_1) \times P(X_1, Y_1) + D(X_2) \times P(X_2, Y_1) + D(X_3) \times P(X_3, Y_1) \ldots P(X_{10}, Y_1)$$

$$Y_2 = D(X_1) \times P(X_1, Y_2) + D(X_2) \times P(X_2, Y_2) + D(X_3) \times P(X_3, Y_2) \ldots P(X_{10}, Y_2)$$

$$Y_3 = D(X_1) \times P(X_1, Y_3) + D(X_2) \times P(X_2, Y_3) + D(X_3) \times P(X_3, Y_3) \ldots P(X_{10}, Y_3)$$

.
.
.

$$Y_9 = D(X_1) \times P(X_1, Y_9) + D(X_2) \times P(X_2, Y_9) + D(X_3) \times P(X_3, Y_9) \ldots P(X_{10}, Y_9)$$

$$Y_{10} = D(X_1) \times P(X_1, Y_{10}) + D(X_2) \times P(X_2, Y_{10}) + D(X_3) \times P(X_3, Y_{10}) \ldots P(X_{10}, Y_{10})$$

DETAILED DESCRIPTION

Figure 1:
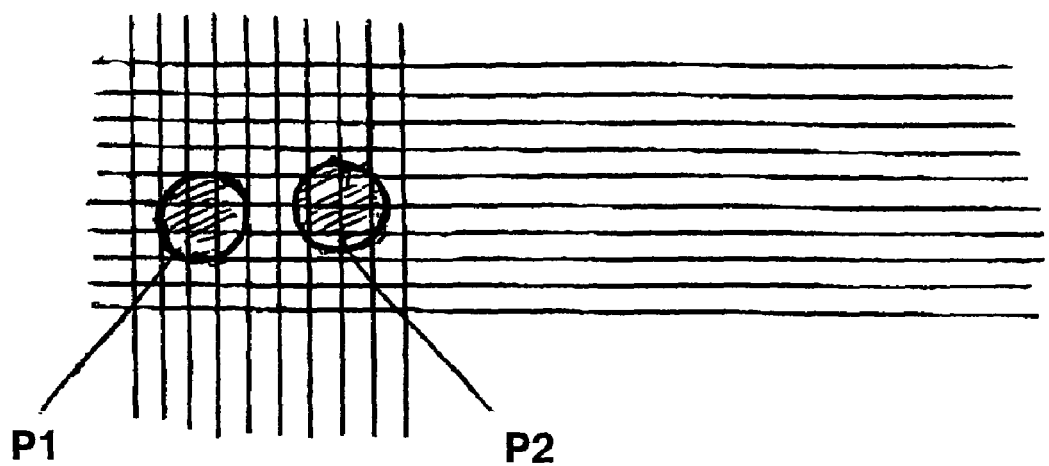
FIG. 1 illustrates two particles of a same size triggering two different pixel counts exemplifying location error.

The invention is a method whereby the magnification of an optical system may be reduced by approximately 5 times from conventional systems and the number of pixels required to be contained within the image of the smallest particle reduced by a factor of approximately 25 times from conventional systems without loss of accuracy in measurement. This reduction in magnification results in a decrease in measurement time by a factor of approximately 15 times, and an increase by a factor of 5 times in the largest particle which may be included in the measurement range.

Description of the Method

The method depends on the facts that (a) the total population to be analyzed contains many particles and is uniformly distributed, over many frames, throughout the optical sampling volume, and that (b) even when substantial uncertainty exists on the parameter value corresponding any individual image, the statistical information which is obtained from many images may be used to provide accurate distributions.

As noted in FIG. 1, the image of a particle of given parameter size may occupy a different number of pixels depending on its location and on the threshold setting. A first particle P1 occupies 9 pixels at least partially. A second particle P2 occupies 16 pixels at least partially. The particles images are randomly placed on the grid. If a threshold is selected, the probabilities corresponding to each of the possible pixel totals may be computed for a particle of known parameter value. One method of doing this is to establish a geometrical computer model, which successively places particle outlines randomly on a grid equivalent to the pixel array and determines count outcomes for any threshold level.

By way of example, a computer is programmed to simulate a coin toss onto a grid of squares, wherein the coin is larger than a single square, such that the coin placed over the grid could overlap 9 squares or more depending on how the coin is positioned over the squares. The same coin that occupied 9 squares could also occupy 10, 11, 12 and up to 16 squares, depending upon where it lands on the grid. Each time the simulation occurs, the coin will cover at least a portion of a plurality of squares on the grid by simulating the tossing of it onto a random location within a predetermined range. Therefore, the computer simulates the random tossing of a token, for example in the shape of a coin, onto a grid or array of squares. The computer is then programmed to determine the number of full and partial grid locations or squares that are covered. This is repeatedly done many thousands of times, until enough data is collected to determine statistically, the probability that n, n+1, n+2 . . . n+m squares will be covered, where n is a number that corresponds to the least number of squares that can be at least partially covered by the token. Although in this example a token such as a coin-like object is used in the simulation, other polygons may be used in the simulation The computer is also programmed to respond to different thresholds so that a minimum area of a square must be covered in order for the computer program to count the square as being covered. By way of example, if the threshold is set to one half of a square equivalent to 50% of full intensity detected by a detector in the real system, then, when less than a half square is covered, the computer does not count an occurrence of that square being covered.

Random number generators such as those based on generating random or pseudo-random numbers in dependence of detecting noise, could be used in this computer system to randomly locate the token on the grid. U.S. Pat. No. 6,324,558 in the name of Wilber issued Nov. 27, 2001 incorporated herein by reference describes an inexpensive convenient circuit, which can be coupled to a parallel port of a computer for generating random numbers.

The method of determining a distribution of a parameter of a particle population in accordance with this invention shall now be described. The parameter may be one of several possible parameters; for example cross-section, shape, or a particular bacteria, which corresponds to a predetermined cross-section range. For example bacteria B is known to be within a predetermined size range. Hence, detecting the numbers of bacteria B in a sample may be the desired goal.

Prior to running the simulation the step size in the parameter of interest must be determined and input as data into the simulator. For example, it may be of interest to find the total number of particles having a diameter of 5.51, 5.52, 5.53, 5.54, . . . 6.0 units in size, or alternatively it may only be required to determine the total number of particles within the volume sampled having parameter value 5.0, 6.0, . . . 8.0 units in size. Rounding in this fashion is done if a less precision is required.

The following expressions and variables illustrate the process in accordance with this invention, of determining a distribution of parameter value $X_M$;

$X_1, X_2, \ldots$ are the steps in the parameter value of interest $Y_1, Y_2, \ldots$ are the counts recorded in the sample run for each pixel total $P(X_M;Y_N)$=the probability of a particle with parameter value $X_M$ occupying pixel total $Y_N$ $D(X_M)$=the total number of particles within the volume sampled having parameter value $X_M$. This is the final information required by the user.

a. A threshold for the run is selected.
b. Using this threshold, a table is computed of $P(X_M;Y_N)$ which relates values of the parameter of interest, in increments $(X_1, X_2 \ldots)$, to the probabilities of occupying the different pixel totals $(Y_1, Y_2, \ldots)$ possible for this parameter value, for example a 3.1 micron diameter particle image occupies 12 pixels with probability 0.1, 13 pixels with probability 0.24, . . . , a 3.2 micron particle occupies 12 pixels with probability 0.05, . . .
c. The total number of counts for any pixel total is a sum of the products of the concentrations of particles having each parameter value which can occupy this pixel total and the probability of such a particle occupying this total. A series of linear equations is constructed.

$Y_1=D(X_1) \times P(X_1,Y_1)+D(X_2) \times P(X_2,Y_1)+$ $Y_2=D(X_1) \times P(X_1,Y_2)+D(X_2) \times P(X_2,Y_2)+$ The series is continued until the pixel total is sufficiently large that location errors are acceptable without correction. This set of equations is solved using recursive techniques to provide the values of $D(X_M)$.

Of course, numerous other embodiments may be envisaged, without departing from the spirit and scope of the invention.

What is claimed is:

1. A method for determining a distribution of a parameter of a particle population comprising the steps of:
   a) detecting on a pixel array of elements a plurality of images of particles in the particle population;
   b) determining a number of pixels at least partially covered by each particle to form a pixel count for each of the plurality of images of the particles;
   c) obtaining a plurality of weighting factors, which are the probabilities relating each pixel count to parameter values; and,
   d) utilising the pixel counts and the weighting factors to determine the distribution for the parameter of the particle population.

2. A method as defined in claim 1, wherein step (a) includes selecting an acceptable threshold for detecting the presence of a portion of a particle on an array element, and wherein step (c) includes the step of determining said weighting factors.

3. A method as defined in claim 1, wherein step (b) further includes the step of rounding such that particles of a plurality of proximate sizes will be included in each pixel count.

4. A method as defined in claim 1, wherein step (c) is performed by using a model, which successively places particle outlines randomly on a grid equivalent to the pixel array and determines pixel count outcomes, for predetermining the probabilities relating each pixel count to a parameter value.

5. A method as defined in claim 4, further comprising inputting into said model information related to the shape of said detected images of particles.

6. A method as defined in claim 4, wherein the characteristic is the cross-sectional area of the particles in the particle population.

7. A method as claimed in claim 1, wherein the parameter is the cross-sectional area of the particles in the particle population.

8. A method as defined in claim 1, wherein step (d) includes the steps of:
   i) utilizing said pixel counts and said weighting factors to construct a set of linear equations, and
   ii) solving said set of linear equations to determine said distribution of the parameter of said particle population.

9. In a system for analyzing a parameter in a particle population in a fluid, wherein particles are substantially randomly distributed, and particles range in value from $X_1$ to $X_{10}$, in increments, values of $X_1$ through $X_{10}$ being different values, a method of determining a total number of particles within a sampled volume having a predetermined parameter value, comprising the steps of:
   a) using a detector array of pixels to detect a plurality of images of the particles;
   b) counting a number of pixels $Y_1, Y_2, Y_3$, through at least $Y_{10}$ corresponding to each of the plurality of images of particles;
   c) determining a plurality of weighting factors $P(X_M;Y_N)$ corresponding to different pixel counts from $Y_1$ through at least $Y_{10}$, wherein $P(X_M;Y_N)$=the probability of a particle with a parameter value $X_M$ will occupy a pixel total $Y_N$, wherein M can take on values from 1 rough at least 10 and X can take on values from at least 1 through 10
   d) determining $D(X_M)$=the total number of particles within the volume sampled having a parameter value $X_M$, by solving a set of linear equations of the form:

$Y_1=D(X_1) \times P(X_1,Y_1)+D(X_2) \times P(X_2,Y_1)+D(X_3) \times P(X_3,Y_1) \ldots P(X_{10},Y_1)$ $Y_2=D(X_1) \times P(X_1,Y_2)+D(X_2) \times P(X_2,Y_2)+D(X_3) \times P(X_3,Y_2) \ldots P(X_{10},Y_2)$

.

.

.

$Y_{10}=D(X_1) \times P(X_1,Y_{10})+D(X_2) \times P(X_2,Y_{10})+D(X_3) \times P(X_3,Y_{10}) \ldots P(X_{10},Y_{10})$.

* * * * *